(12) United States Patent
Carreira

(10) Patent No.: US 7,790,900 B2
(45) Date of Patent: Sep. 7, 2010

(54) METHOD FOR PRODUCING AN OPTICALLY ACTIVE NITRO COMPOUND

(75) Inventor: Erick M. Carreira, c/o Laboratory of Organic Chemistry, ETH-Hoenggerberg, Zurich (CH)

(73) Assignees: Sumitomo Chemical Company, Limited, Tokyo (JP); Erick M. Carreira, Zurich (CH)

( * ) Notice: Subject to any disclaimer, the term of this patent is extended or adjusted under 35 U.S.C. 154(b) by 919 days.

(21) Appl. No.: 10/556,777

(22) PCT Filed: May 17, 2004

(86) PCT No.: PCT/JP2004/006984

§ 371 (c)(1),
(2), (4) Date: Nov. 15, 2005

(87) PCT Pub. No.: WO2004/103951

PCT Pub. Date: Dec. 2, 2004

(65) Prior Publication Data

US 2007/0037976 A1 Feb. 15, 2007

(30) Foreign Application Priority Data

May 23, 2003 (JP) .............................. 2003-145950

(51) Int. Cl.
*C07D 213/00* (2006.01)
*C07C 211/00* (2006.01)
*C07D 307/02* (2006.01)
*C07D 333/12* (2006.01)
*C07D 315/00* (2006.01)

(52) U.S. Cl. ................. 546/329; 564/305; 549/491; 549/74; 549/497; 549/419

(58) Field of Classification Search .............. 564/305; 546/329; 549/491, 74, 497, 419
See application file for complete search history.

(56) References Cited

U.S. PATENT DOCUMENTS 6,465,664 B1 10/2002 Buchwald et al.

FOREIGN PATENT DOCUMENTS

WO WO 92/09545 A 6/1992
WO WO 02/66417 A 8/2002

OTHER PUBLICATIONS

"A General Method for the Preparation of 2,2-Disubstituted 1-Nitroalkenes", J. Org. Chem. 1993, 58, 3850-3856.*
Paul Knochel, et al., "Synthesis and Reactivity toward Aeyl Chlorides and Enones of the New Highly Functionalized Copper Reagents $RC_u(CN)ZnI$", J. Org. Chem., 1988, vol. 53, No. 10, pp. 2390-2392.
Carreira, E.M. et al., "Catalytic enantioselective conjugate reduction of beta,beta-disubstituted nitroalkenes", Angew. Chem. Int. Ed., vol. 42, No. 39, Oct. 13, 2003, pp. 4793-4795.
Crosby, S.R. et al., Tetrahedron Lett., vol. 41, No. 3, 2000, pp. 397-402. Database Accession No. 5343173.
Eilitz, U. et al., Tetrahedron, vol. 14, No. 2, 2003, pp. 189-192. Database Accession No. 9274082 abstract.
Enders, D. et al., Eur. J. Org. Chem., vol. 9, 1998, pp. 1771-1792. Database Accession No. 5168067 abstract.
Iseki, K. et al., Tetrahedron Lett., vol. 37, No. 0, 1996, pp. 9081-9084. Database Accession No. 4657206 abstract.
Lawrence, N. J. et al., "Polymethylhydrosiloxane: a versatile reducing agent for organic synthesis" J. Chem. Soc. Perkin Trans. 1, 1999, pp. 3381-3391.
Magnus, P. et al., "Direct conversion of alpha,beta-unsaturated nitriles into cyanohydrins using Mn(dpm)3 catalyst, dioxygen and phenylsilane", Tetrahedron Letters, vol. 42, No. 25, Jun. 18, 2001, pp. 4127-4129.
Ongeri, S. et al., "Optimization of new chiral ligands for the copper-catalysed enantioselective conjugate addition of Et2Zn to nitroolefins by high-throughput screening of a parallel library", Eur. J. Org. Chem., 2001, pp. 803-807.
Schaefer, H. et al., Tetrahedron, vol. 51, No. 8, 1995, pp. 2305-2324. Database Accession No. 4199910 abstract.
Trost, B.M. et al., Angew. Chem. Int. Ed., vol. 41, No. 5, 2002, pp. 861-863. Database Accession No. 9020738 abstract.
Yuasa, Y. et al., Synth. Commun., vol. 28, No. 3, 1998, pp. 395-402. Database Accession No. 4893618 abstract.

* cited by examiner

*Primary Examiner*—Janet L Andres
*Assistant Examiner*—Binta M Robinson
(74) *Attorney, Agent, or Firm*—Foley & Lardner LLP

(57) ABSTRACT

An optically active nitro compound having two hydrogen atoms on its α-carbon atom and having β-asymmetric carbon atom can be produced by making α,β-unsaturated nitroolefin having a hydrogen atom on its α-carbon atom react with at least two organosilicon compounds having at least one silicon-hydrogen bond in the molecule in the presence of an asymmetric copper complex, or react with an organosilicon compound having at least one silicon-hydrogen bond in the molecule in the presence of an asymmetric copper complex and water.

11 Claims, No Drawings

METHOD FOR PRODUCING AN OPTICALLY ACTIVE NITRO COMPOUND

TECHNICAL FIELD

The present invention relates to a method for producing an optically active nitro compound and amino compound.

BACKGROUND ARTS

Optically active nitro compounds and amino compounds are useful for synthetic intermediates for fine chemicals, medicaments, pesticides and so on.

U.S. Pat. No. 6,456,664 discloses a process for producing optically active compounds having an electron-withdrawing group by reducing olefin with a silicon compound in the presence of an asymmetric copper complex. Said electron-withdrawing groups generally include nitro group, however the process gives poor yield when the process is applied to nitro compounds. Further, it may cause side reaction of isomerization.

DISCLOSURE OF THE INVENTION

The present invention provides a method for producing an optically active nitro compound having two hydrogen atoms on its α-carbon atom and having β-asymmetric carbon atom which comprises making α,β-unsaturated nitroolefin having a hydrogen atom on its α-carbon atom react with at least two organosilicon compounds having at least one silicon-hydrogen bond in the molecule in the presence of an asymmetric copper complex.

Further, the present invention provides a method for producing an optically active nitro compound having two hydrogen atoms on its α-carbon atom and having β-asymmetric carbon atom which comprises making α,β-unsaturated nitroolefin having a hydrogen atom on its α-carbon atom react with an organosilicon compound having at least one silicon-hydrogen bond in the molecule in the presence of an asymmetric copper complex and water.

Furthermore, the present invention provides a method for producing an optically active amino compound which comprises reducing the nitro compound obtained by the above-mentioned methods.

The optically active nitro compounds having two hydrogen atoms on its α-carbon atom and having β-asymmetric carbon atom are given by formula:

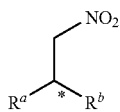

wherein $R^a$ and $R^b$ are different from each other and represent organic groups which are inert to the reduction of a nitro compound, and * indicates an asymmetric carbon.

The α,β-unsaturated nitroolefins having a hydrogen atom on its α-carbon atom of formula:

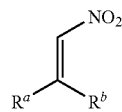

wherein $R^a$ and $R^b$ have the same meanings given above, are utilized for the present invention.

Typical compounds of the optically active nitro compound are given by formula (1):

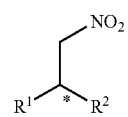

(1)

wherein $R^1$ and $R^2$ are different from each other, and each of $R^1$ and $R^2$ represents an optionally substituted C1-C10 alkyl group, optionally substituted C3-C10 cycloalkyl group, optionally substituted C6-C14 aryl group or optionally substituted heterocyclic group; said heterocyclic group is pyridyl group, pyrimidinyl group, furyl group, thienyl group, pyrazolyl group, imidazolyl group, oxazolyl group, thiazolyl group, quinolyl, quinazolinyl, dihydropyridyl, tetrahydrofuranyl and piperidyl group; and the substituent of the alkyl group, cycloalkyl group, aryl group and heterocyclic group is one or more selected from the group consisting of halogen atom, hydroxyl group, cyano group, isocyano group, C1-C10 alkoxy group, C3-C10 cycloalkyl group, C6-C14 aryl group, C1-C10 alkylcarbonyl group, C6-C14 haloaryl group, C1-C10 alkylcarbonyloxy group, benzyloxy group, halobenzyloxy group, C1-C10 alkylsulfonyloxy group, C6-C14 arylsulfonyloxy group, C6-C14 haloarylsulfonyloxy group, tetrahydrofuranyloxy group, tetrahydropyranyloxy group, amino group, C1-C10 alkylcarbonylamino group, trifluoroacetamino group, C6-C14 arylcarbonylamino group, halobenzoylamino group, benzyloxycarbonylamino group, pyridyl group, pyrimidinyl group, furyl group, thienyl group, imidazolyl group, halopyridyl group, C1-C10 alkylpyridyl group and C1-C10 alkylfuryl group, and * indicates an asymmetric carbon, and typical compounds of the α,β-unsaturated nitroolefins having a hydrogen atom on its α-carbon atom are given by formula (2):

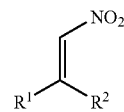

(2)

wherein $R^1$ and $R^2$ have the same meanings given above.

Examples of the C1-C10 alkyl group for the optionally substituted C1-C10 alkyl group, C1-C10 alkylcarbonyl group, C1-C10 alkylcarbonyloxy group, C1-C10 alkylsulfonyloxy group, C1-C10 alkylcarbonylamino group, C1-C10 alkylpyridyl group and C1-C10 alkylfuryl group include methyl, ethyl, propyl, isopropyl, butyl, isobutyl, sec-butyl, tert-butyl, pentyl and hexyl.

Examples of the C3-C10 cycloalkyl group for the optionally substituted C3-C10 cycloalkyl group and C3-C10 cycloalkyl group as the substituent include cyclopropyl, cyclopentyl, cyclohexyl and cyclooctyl.

Examples of the C6-C14 aryl group for the optionally substituted C6-C14 aryl group, C6-C14 aryl group as the substituent, C6-C14 arylsulfonyloxy group and C6-C14 arylcarbonylamino group include phenyl, 3-methylphenyl, 4-methylphenyl, 2,4-dimethylphenyl, 2,6-dimethylphenyl, 1-naphthyl and 2-naphthyl.

Examples of the heterocyclic group include 2-pyridyl group, 3-pyridyl group, 4-pyridyl group, 2-pyrimidinyl group, 4-pyrimidinyl group, 5-pyrimidinyl group, 2-furyl group, 3-furyl group, 2-thienyl group, 3-thienyl group, 1-pyrazolyl group, 3-pyrazolyl group, 1-imidazolyl group, 2-imidazolyl group 4-imidazolyl group, 2-oxazolyl group, 2-thiazolyl, 2-quinolyl, 8-quinolyl, 2-quinazolinyl, 1,4-dihydro-2-pyridyl, tetrahydrofuranyl and 2-piperidyl group which may be substituted.

The substituents of the alkyl, cycloalkyl, aryl and heterocyclic group are explained in detail below.

Examples of the halogen atom include fluorine, chlorine, bromine and iodine; examples of the C1-C10 alkoxy group include methoxy, ethoxy and butoxy; and examples of the C1-C10 alkylcarbonyl group include acetyl and propionyl. The C6-C14 haloaryl group means C6-C14 aryl group substituted by one or more halogen atoms and the typical examples include 4-chlorophenyl, 3-fluorophenyl, 2,4-dichlorophenyl, 2,6-dichlorophenyl and 4-trifluoromethylphenyl. Examples of the C1-C10 alkylcarbonyloxy group include acetoxy and propionyloxy. The halobenzyloxy group means benzyloxy group substituted by one or more halogen atoms and the typical examples include 4-chlorobenzyloxy and 3-fluorobenzyloxy; and examples of the C1-C10 alkylsulfonyloxy group include methanesulfonyloxy and ethanesulfonyloxy; examples of the C6-C14 arylsulfonyloxy group include benzenesulfonyloxy, 4-methylbenzenesulfonyloxy and naphthalenesulfonyloxy. The C6-C14 haloarylsulfonyloxy group means C6-C14 arylsulfonyloxy group substituted by one or more halogen atoms and the typical examples include 4-chlorobenzenesulfonyloxy and 4-bromobenzenesulfonyloxy. Examples of the C1-C10 alkylcarbonylamino group include acetamino and propionamino; and examples of the C6-C14 arylcarbonylamino group include benzoylamino, 4-methylbenzoylamino and naphthylamino. The halobenzoylamino group means benzoylamino group substituted by one or more halogen atoms and the typical examples include 4-chlorobenzoylamino and 3-fluorobenzoylamino. Examples of the pyridyl group include 2-pyridyl, 3-pyridyl and 4-pyridyl; examples of the pyrimidinyl group include 2-pyrimidinyl, 4-pyrimidinyl and 5-pyrimidinyl; examples of the furyl group include 2-furyl and 3-furyl; examples of the thienyl group include 2-thienyl and 3-thienyl; and examples of the imidazolyl group include 1-imidazolyl, 2-imidazolyl and 4-imidazolyl. The halopyridyl group means pyridyl group substituted by one or more halogen atoms and the typical examples include 5-chloropyridin-2-yl, 3,5-dichloropyridin-2-yl and 5-bromopyridin-3-yl. Examples of the C1-C10 alkylpyridyl group include 5-methylpyridin-2-yl and 6-methylpyridin-2-yl; and examples of the C1-C10 alkylfuryl group include 5-methyl-2-furyl and 3-methyl-2-furyl.

Examples of the optionally substituted C1-C10 alkyl group for $R^1$ and $R^2$ include methyl, ethyl, propyl, isopropyl, butyl, isobutyl, sec-butyl, tert-butyl, pentyl, hexyl, chloromethyl, trifluoromethyl, hydroxymethyl, 1-hydroxy-1-methylethyl, cyanomethyl, isocyanomethyl, methoxymethyl, ethoxymethyl, benzyl, phenethyl, 4-methylbenzyl, acetonyl, 3,3-dimethyl-2-oxo-butyl, 4-chlorobenzyl, 2,6-dichlorobenzyl, 4-trifluoromethylbenzyl, acetoxymethyl, benzyloxymethyl, 4-chlorobenzyloxymethyl, 2,4-dichlorobenzyloxymethyl, methanesulfonyloxymethyl, benzenesulfonyloxymethyl, 4-methylbenzenesulfonyloxymethyl, 4-chlorobenzenesulfonyloxymethyl, tetrahydrofuranyloxymethyl, tetrahydropyranyloxymethyl, aminomethyl, acetaminomethyl, trifluoroacetaminomethyl, benzoylaminomethyl, 4-chlorobenzoylaminomethyl, benzyloxycarbonylaminomethyl, pyridin-2-ylmethyl, pyrimidin-2-ylmethyl, furfuryl, thiophen-2-ylmethyl, imidazol-1-ylmethyl, 5-chloropyridin-2-ylmethyl, 6-methylpyridin-2-ylmethyl and 5-methylfurfuryl.

Examples of the optionally substituted C3-C10 cycloalkyl group for $R^1$ and $R^2$ include cyclopropyl, cyclopentyl, cyclohexyl and cyclooctyl, 2,2-dichlorocyclopropyl, 4-chlorocyclohexyl, 2,2-dicyanocyclopropyl, 4-cyanocyclohexyl and 4-isocyanocyclohexyl.

Examples of the optionally substituted C6-C14 aryl group for $R^1$ and $R^2$ include phenyl, 3-methylphenyl, 4-methylphenyl, 2,4-dimethylphenyl, 2,6-dimethylphenyl, 1-naphthyl, 2-naphthyl, 4-chlorophenyl, 3-fluorophenyl, 4-trifluoromethylphenyl, 4-hydroxyphenyl, 4-cyanophenyl, 4-isocyanophenyl, 4-methoxyphenyl, 4-tert-butoxyphenyl, 4-phenylphenyl, 4-acetylphenyl, 4-aminophenyl and 4-acetaminophenyl.

Examples of the optionally substituted heterocyclic group for $R^1$ and $R^2$ include 2-pyridyl, 3-pyridyl, 4-pyridyl, 2-pyrimidinyl, 4-pyrimidinyl, 5-pyrimidinyl, 2-furyl, 3-furyl, 2-thienyl, 3-thienyl, 1-imidazolyl, 2-imidazolyl, 4-imidazolyl, 5-chloropyridin-2-yl, 3,5-dichloropyridin-2-yl, 5-bromopyridin-3-yl, 5-methylpyridin-2-yl, 6-methylpyridin-2-yl, 4-cyanopyridin-2-yl, 2-quinolyl, 8-quinolyl, 2-quinazolinyl, 5-methyl-2-furyl and 3-methyl-2-furyl.

The α,β-unsaturated nitroolefin having a hydrogen atom on its α-carbon atom used for the reaction of the present invention can be prepared by the reaction of nitromethane with a ketone (nitro-aldol reaction, Henry reaction) optionally followed by dehydration of the obtained nitroalcohol, or prepared by the reaction of an olefin with dinitrogen tetraoxide followed by elimination reaction. The preparation of the nitroolefin are well known and referred to many literatures including N. Ono "The Nitro Group in Organic Synthesis" Wiley-VCH, New York, pp. 30-44 (2001) and Synthesis, p. 1017-1018 (1982).

Both (E)- and (Z)-nitroolefins can be utilized for the present invention.

The asymmetric copper complex used for the present invention is prepared by copper salt and optically active ligand precursor.

Examples of the copper salt include copper alkoxides such as copper C1-C6 alkoxides (e.g. copper tert-butoxide), copper carboxylates such as copper C2-C6 carboxylates (e.g. copper acetate) and copper trifluoroacetate, copper sulfonates (e.g. copper trifluoromethanesulfonate), copper halides such as copper chloride and copper bromide, copper sulfate, copper tetrafluoroborate, copper trifluoromethanesulfonamide and copper phosphate. Both of cuprous (Cu(I)) salts and cupric (Cu(II)) salts are available as copper salts, however, cuprous salts are preferable. Further, cuprous alkoxides, especially, cuprous tert-butoxide is preferable. Cuprous alkoxide is prepared by the reaction of cuprous halide with sodium alkoxide, and it is provided to the reaction.

Examples of the optically active ligand precursor include optically active phosphorus-phosphorus ligand (bidentate phosphine ligand) such as optically active 2,2'-bis(diphenylphosphino)-1,1'-binaphthyl (optically active BINAP), optically active 6,6'-dimethyl-2,2'-bis(diphenylphosphino)-1,1'-biphenyl (optically active BIPHEMS), optically active 2,2'-bis(di-p-tolylphosphino)-1,1'-binaphthyl (optically active p-tol-BINAP), optically active N-(tert-butoxycarbonyl)-4-(diphenylphosphino)-2-[(diphenylphosphino)methyl] pyrrolidine (optically active BPPM), optically active 2,3-o-isopropylidene-2,3-dihydroxy-1,4-bis(diphenylphosphino) butane (optically active DIOP), optically active 2,3-bis (diphenylphosphino)butane (optically active CHIRAPHOS), optically active 2,4-bis(diphenylphosphino)pentane (optically active BDPP), optically active 5,6-bis(diphenylphosphino)-2-norbornene (optically active NORPHOS), optically active 1-[1',2-bis(diphenylphosphino)ferrocenyl]ethyl alcohol (optically active BPPFOH), optically active 1,2-bis(2,5-diethylphosphorano)ethane (optically active Et-BPE), optically active 1,2-bis(2,5-dimethylphosphorano)benzene (optically active Me-DUPHOS), optically active 1-[2-(diphenylphosphino)ferrocenyl]ethyldicyclohexylphosphine (optically active JOSIPHOS), optically active 6,6'-dimethoxybiphenyl-2,2'-diylbis[di(3,5-di-tert-butylphenyl)phosphine] (optically active 3,5-tBu-MeO-BIPHEP), optically active 6,6'-dimethoxybiphenyl-2,2'-diylbis[di(2-furyl)phosphine] (optically active 2-Furyl-MeO-BIPHEP) and optically active 1-[2-(dicyclohexylphosphino) ferrocenyl]ethyldicyclohexylphosphine; optically active phosphorus-nitrogen ligand (bidentate phosphinite ligand) such as optically active methyl α-glucopyranoside-2,6-dibenzoate-3,4-di[bis(3,5-dimethylphenyl) phosphinite], optically active 1,2-cyclohexyldiamino-N,N'-bis(2-diphenylphosphanylbenzamide) and optically active 2-(2-diphenylphosphanylferrocenyl)-4-isopropyl-4,5-dihydrooxazol; optically active phosphorus-sulfur ligand such as diphenyl-2-(2'-phenylsulfenyl-[1,1']-binaphthalen-2-yl)phosphane and optically active 2-(1-methylsulfenylethyl)-1-(diphenylphosphanyl)ferrocene; optically active nitrogen-nitrogen ligand such as optically active 2,2'-isopropylidene-bis(4-benzyl-2-oxazoline), optically active bis(4-tert-butyl-4,5-dihydrooxazol-2-yl)phenylamine, optically active 4,4'-dibenzyl-4,5,4',5'-tetrahydro-[2,2']-bioxazolyl, optically active (4-phenyl-4,5-dihydrooxazol-2-yl)-[4-phenyloxazolidin-(2E)-ylidene] acetonitrile and optically active 2,6-bis(4-isopropyl-2-oxazolin-2-yl)pyridine; and optically active carbon ligand such as optically active 2-[(3N-methylimidazol-1-yl)methyl]-1-trimethylsilylferrocene. Among them, optically active bidentate phosphine ligand is preferably used. Further, optically active p-tol-BINAP, optically active JOSIPHOS and 3,5-tBu-MeO-BIPHEP are more preferable.

The optically active ligand precursors have optical isomers, for example, p-tol-BINAP has two optical isomers of (S)-p-tol-BINAP and (R)-p-tol-BINAP. Each of the optically active ligand precursors can be used for the objective optically active nitro compound having two hydrogen atoms on its α-carbon atom and having β-asymmetric carbon atom These optically active ligand precursors are available in the market and also prepared by known methods described in R. Noyori "Asymmetric Catalysis in Organic Synthesis" John Wiley & Sons, New York (1994), Chapter 2; I Ojima "Catalytic Asymmetric Synthesis" VCH Publishers, New York (1993), Chapter 1; J. Am. Chem. Soc., 116, 4062-4066 (1994) and so on.

The asymmetric copper complex is usually prepared by mixing the copper salt with the optically active ligand precursor in an inert solvent such as aromatic hydrocarbons (e.g. toluene, xylene). In the preparation, the amount of the optically active ligand precursor is usually equimolecular or more to the copper salt. Too much ligand precursor may not be beneficial by economical reason. Thus, the amount of the ligand precursor is usually 1 to 2 parts, preferably 1 to 1.5 parts by mol to 1 part by mol of the copper salt.

The mixture of the optically active ligand precursor and the copper salt in the solvent can be used as it is, or the mixture is concentrated and then provided for the reaction of the present invention. Further, the asymmetric copper complex may be formed in the reaction vessel of the α,β-unsaturated nitroolefin having a hydrogen atom on its α-carbon atom by adding the optically active ligand precursor and the copper salt separately.

The amount of the asymmetric copper complex is, based on the amount of the copper salt, usually 0.0001 to 0.5 part, preferably 0.0005 to 0.3 part by mol to 1 part by mol of the nitroolefin.

Examples of the organosilicon compounds having at least one silicon-hydrogen bond in the molecule used for the reaction of the present invention include poly(methylhydrosiloxane), hydride terminated poly(dimethylsiloxane), 1,1,3,3-tetramethyldisiloxane, 1,1,1,3,5,5,5-heptamethyltrisiloxane, tris(dimethylsilyloxy)methylsilane, tris(trimethylsilyloxy) silane, tetrakis(dimethylsilyloxy)silane, trimethoxysilane, triethoxysilane, phenylsilane, methylphenylsilane, diphenylsilane, diphenylmethylsilane, triphenylsilane, dimethylphenylsilane, 1,2-bis(dimethylsilyl)benzene and 1,4-bis(dimethylsilyl)benzene.

According to the first method of the present invention, the optically active nitro compound having two hydrogen atoms on its α-carbon atom and having β-asymmetric carbon atom can be produced by making α,β-unsaturated nitroolefin having a hydrogen atom on its α-carbon atom react with at least two organosilicon compounds having at least one silicon-hydrogen bond in the molecule in the presence of an asymmetric copper complex.

The optically active nitro compound, nitroolefin, organosilicon compound and asymmetric copper complex are mentioned above.

In the method, two or mote kinds of the organosilicon compound are utilized. Typical combination is poly(methylhydrosiloxane) and at least one selected from the group consisting of phenylsilane, diphenylsilane and dimethylphenylsilane. In such case, the mixing ratio by mol of the poly(methylhydrosiloxane) to the phenylsilane, diphenylsilane and dimethylphenylsilane is usually 1 to 0.1-50, preferably 1 to 0.3-25.

The reaction is usually carried out at −78 to 100° C., preferably 0 to 50° C. The reaction time is usually 0.5 to 50 hours. The total amount of the organosilicon compounds used for the reaction is usually 1-10 parts by mol to 1 part by mol of the nitroolefin.

The reaction is usually carried out in an inert solvent. Examples of the solvent for the reaction include aromatic hydrocarbons such as toluene and xylene; ethers such as diethyl ether, methyl tert-butyl ether and tetrahydrofuran; aliphatic hydrocarbons such as hexane and heptane; halogenated hydrocarbons such as dichloromethane, chloroform and chlorobenzene; esters such as ethyl acetate; nitriles such as acetonitrile; ketones such as acetone; water and mixtures thereof. The solvent may be degassed of oxygen or air, under inert gas such as nitrogen and argon.

After the reaction, usual work-up procedure gives the objective optically active nitro compound. The reaction mixture is typically mixed with aqueous tetrabutylammonium fluoride solution, optionally added lipophilic organic solvent, extracted with the organic solvent and concentrated the organic layer to give the nitro compound. Examples of the organic solvent include aromatic hydrocarbons such as toluene and xylene; aliphatic hydrocarbons such as hexane and heptane; halogenated hydrocarbons such as dichloromethane, chloroform, chlorobenzene and dichlorobenzene; and ethers such as diethyl ether and methyl tert-butyl ether. The isolated nitro compound can be purified by usual procedures such as distillation, recrystallization and so on. When the objective compound is the optically active amino compound corresponding to the nitro compound, the reaction mixture can be subjected to the following reduction procedure without isolation.

According to the second method of the present invention, the optically active nitro compound having two hydrogen atoms on its α-carbon atom and having β-asymmetric carbon atom can be produced by making α,β-unsaturated nitroolefin having a hydrogen atom on its α-carbon atom react with an organosilicon compound having at least one silicon-hydrogen bond in the molecule in the presence of an asymmetric copper complex and water.

The optically active nitro compound, nitroolefin, organosilicon compound and asymmetric copper complex are mentioned above.

In this method, one kind of the organosilicon compound is sufficient for the reaction, though two or more kinds of the organosilicon compounds can be used. The amount of the organosilicon compound used for the reaction is usually 1-10 parts by mol to 1 part by mol of the nitroolefin.

The amount of water used for the reaction is usually one or more parts by mol to 1 part by mol of the nitroolefin. Water may be used in a large excess amount as a reaction solvent.

This method is usually carried out in a solvent and the solvent for the reaction is the same as the solvent for the reaction in the first method. The method is usually carried out by mixing the optically active nitro compound, organosilicon compound, asymmetric copper complex and water in the solvent, and the mixing order is not restricted. The reaction temperature and reaction time are the same as the first method. Further, the work-up procedures after the reaction are the same as the first method.

Examples of the optically active nitro compound produced by the first or second method include optically active compounds of 1-nitro-2-phenylpropane, 2-(4-methylphenyl)-1-nitropropane, 2-(4-chlorophenyl)-1-nitropropane, 2-(4-methoxyphenyl)-1-nitropropane, 2-(4-acetylphenyl)-1-nitropropane, 1-nitro-2-(4-trifluoromethylphenyl)propane, 3-methyl-1-nitro-2-phenylbutane, 3-hydroxy-1-nitro-2-phenylpropane, 1-nitro-2,3,3-trimethylbutane, 3-hydroxy-2,3-dimethyl-1-nitrobutane, 2,4,4-trimethyl-1-nitropentane, 1-nitro-2-phenylpentane, 2-(2-naphthyl)-1-nitropropane, 3-(benzoylamino)-1-nitro-2-phenylpropane, 3-acetamino-1-nitro-2-phenylpropane, 3-(trifluoroacetamino)-1-nitro-2-phenylpropane, 1-nitro-2-(pyridin-2-yl)propane, 2-(5-chloropyridin-2-yl)-1-nitropropane, 1-nitro-2-[(pyridin-2-yl)methyl]propane, 2-(furan-2-yl)-1-nitropropane, 2-furfuyl-1-nitropropane, 1-nitro-2-(thiophen-2-yl)propane, 1-nitro-2-[(tetrahydropyranyloxy)methyl]propane and 1-nitro-2-[(tetrahydrofurfuryloxy)methyl]propane.

The optically active nitro compound produced by the first or second method can be subjected to a reduction process to provide an optically active amino compound, which has two hydrogen atoms on its α-carbon atom and has β-asymmetric carbon atom. The nitro compound can be subjected to a reduction process without isolation, namely the reaction mixture can be subjected as it is after the reaction of the first or second method.

Typical example of the optically active amino compound is given by formula (3):

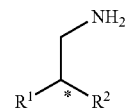

(3)

wherein $R^1$ and $R^2$ have the same meanings given above, and * indicates an asymmetric carbon, which is produced by the reduction of the optically active nitro compound given by formula (1).

The reduction process is carried out according to a known method for reducing nitro group to amino group.

Typical method is reduction by hydrogen donor such as hydrogen, formic acid and ammonium formate in the presence of a metal catalyst. Examples of the metal catalyst include noble metals such as palladium, ruthenium and platinum, and Raney nickel. Both of heterogeneous catalysts and homogeneous catalysts are available as the noble metal catalyst, however, heterogeneous catalysts are preferable because the recovery of the catalyst is easy. In the noble metal heterogeneous catalysts, the noble metal is supported on a suitable carrier such as activated carbon, silica and zeolite. The amount of the noble metal on the carrier is usually 0.1-20 parts, preferably 0.2-10 parts by weight to 100 parts by weight of the carrier. A carrier having a larger surface area is preferably used because it has higher reactivity. The noble metal supported on activated carbon is preferably used.

The amount of the noble metal used for the reduction is usually 0.02-2 parts by weight to the 100 parts by weight of the optically active nitro compound. When Raney nickel is used, the amount of the Raney nickel is usually 1-50 parts by weight to 100 parts by weight of the optically active nitro compound.

The amount of the hydrogen donor is usually 3 parts by mol, practically 10 or more parts by mol to 1 part by mol of the optically active nitro compound.

The reaction is carried out under pressure or at atmospheric pressure. The reaction temperature is usually within the range between −20 and 100° C. and the reaction time is usually within the range between 0.5 and 24 hours.

The reaction is usually carried out in an inert solvent such as alcohol solvents (e.g. methanol, ethanol). When the reaction mixture of the first or second method is used as it is, an addition of the alcohol solvent is preferable.

After the reaction, usual work-up procedure gives the objective optically active amino compound. The reaction mixture is typically subjected to filtration for removing catalyst and then concentration and so on. The isolated amino compound can be purified by distillation, recrystallization and so on. It can also be purified by forming salt (e.g. HCl salt), recrystallization and then making free.

Another typical method is carried out with a reducing agent from nitro group to amino group. Examples of the reducing agent include metal hydrides such as lithium aluminum hydride and sodium borohydride activated by cobalt chloride. The amount of the reducing agent is a theoretical amount or more.

The reducing reaction is usually carried out in an inert solvent such as ethers (e.g. tetrahydrofuran, diethyl ether) and alcohol solvents (e.g. methanol, ethanol). When the reaction mixture of the first or second method is used as it is, an addition of the alcohol solvent is preferable. The reaction temperature is usually within the range between −20 and 100° C. and the reaction time is usually within the range between 0.5 and 24 hours.

After the reaction, usual work-up procedure gives the objective optically active amino compound. The reaction mixture is typically mixed with water or aqueous alkali solution for decomposing the residual reducing agent, extracted with an organic solvent under alkali or neutral condition, and then concentration and so on. The isolated amino compound can be purified by distillation, recrystallization and so on. It can also be purified by forming salt (e.g. HCl salt), recrystallization and then making free.

In the reduction process, the configuration is maintained and the optically active amino compound corresponding to the configuration of the optically active nitro compound is obtained.

Examples of the optically active amino compound produced by the first or second method include optically active compounds of 1-amino-2-phenylpropane, 1-amino-2-(4-methylphenyl)propane, 1-amino-2-(4-chlorophenyl)propane, 1-amino-2-(4-methoxyphenyl)propane, 2-(4-acetylphenyl)-1-aminopropane, 1-amino-2-(4-trifluoromethylphenyl)propane, 1-amino-3-methyl-2-phenylbutane, 1-amino-3-hydroxy-2-phenylpropane, 1-amino-2,3,3-trimethylbutane, 1-amino-3-hydroxy-2,3-dimethylbutane, 1-amino-2,4,4-trimethylpentane, 1-amino-2-phenylpentane, 1-amino-2-(2-naphthyl)propane, 1-amino-3-(benzoylamino)-2-phenylpropane, 3-acetamino-1-amino-2-phenylpropane, 1-amino-3-(trifluoroacetamino)-2-phenylpropane, 1-amino-2-(pyridin-2-yl)propane, 1-amino-2-(5-chloropyridin-2-yl)propane, 1-amino-2-[(pyridin-2-yl)methyl]propane, 1-amino-2-(furan-2-yl)propane, 1-amino-2-furfurylpropane, 1-amino-2-(thiophen-2-yl)propane, 1-amino-2-[(tetrahydropyranyloxy)methyl]propane and 1-amino-2-[(tetrahydrofurfuryloxy)methyl]propane.

EXAMPLES

The present invention will be further illustrated by the following examples; however, the present invention is not limited to these examples. In the following examples, the ratio of (R)/(S) is measured by liquid chromatography analysis with optically active column.

Example 1

In a 10 mL Schlenk-flask, 6.8 mg of cuprous tert-butoxide and 37.3 mg of (S)-p-tol-BINAP were dissolved in 5 ml of toluene. After stirring for 30 minutes at room temperature to give an asymmetric copper complex. One hundred microliters (100 μL) of this solution (containing 1 μmol of the asymmetric copper complex) were mixed with 4.9 ml of toluene, and 90 μL (1.5 mmol) of poly(methylhydrosiloxane) (15-40 mPas (20° C.), d=1.004 g/mL, $n_D^{20}$=1.398, produced by Fluka) and 221 mg (1.2 mmol) of diphenylsilane were added thereto. After stirring for 5 minutes, 1 mmol of (E)-1-nitro-2-phenyl-1-propene was added, and the mixture was further stirred for 24 hours at room temperature. Four milliliters (4 mL) of a tetrahydrofuran solution of tetrabutylammonium fluoride (1 mol/L) were added to the reaction mixture and stirring was continued for 3 hours. Water was added and the mixture was extracted with diethyl ether (30 mL×2). After drying over sodium sulfate, the solvent was evaporated. The residue was purified by flash chromatography (silica gel, hexane/ethyl acetate) to provide optically active 1-nitro-2-phenylpropane.
Yield: 67%
(R)/(S)=86/14

$^1$H-NMR (δ, 300 MHz, CDCl$_3$, 25° C.) 7.34 (m, 2H), 7.25 (m, 3H), 4.58 (dd, J=12.1, 7.5 Hz, 1H), 4.49 (dd, J=12.1, 8.1 Hz, 1H), 3.64 (m, 1H), 1.39 (d, J=6.8 Hz, 3H)

Example 2

In a 10 mL Schlenk-flask, 6.8 mg of copper (I) tert-butoxide and 32.7 mg (55 μmol) of (S)-p-tol-BINAP were dissolved in 5 ml of toluene. After stirring for 30 minutes at room temperature to give an asymmetric copper complex. This solution to the amount containing 1 μmol of the asymmetric copper complex were mixed with 4.9 ml of toluene, and 6 μL (0.1 mmol) of poly(methylhydrosiloxane) (15-40 mPas (20° C.), d=1.004 g/mL, nD20=1.398, produced by Fluka) were added thereto. Further, 185 μL of (1.5 mmol) of phenylsilane and 27 μL (1.5 mmol) of water were added. After stirring for 5 minutes, 1 mmol of (E)-1-nitro-2-phenyl-1-propene was added, and the mixture was further stirred for 24 hours at room temperature. Four milliliters (4 mL) of a tetrahydrofuran solution of tetrabutylammonium fluoride (1 mol/L) were added to the reaction mixture and stirring was continued for 3 hours. Water was added and the mixture was extracted with diethyl ether (30 mL×2). After drying over sodium sulfate, the solvent was evaporated. The residue was purified by flash chromatography (silica gel, hexane/ethyl acetate) to provide optically active 1-nitro-2-phenylpropane.
Yield: 60%
(R)/(S)=89/11

Example 3

The same procedure as Example 2, except that 1 μmol of the asymmetric copper complex of (S)—(R)-JOSIPHOS was used in place of 1 μmol of the asymmetric copper complex of (S)-p-tol-BINAP, provided optically active 1-nitro-2-phenylpropane.
Yield: 77%
(R)/(S)=94/6

Example 4

The same procedure as Example 3, except that (E)-2-(4-chlorophenyl)-1-nitro-1-propene was used in place of (E)-1-nitro-2-phenyl-1-propene, provided optically active 2-(4-chlorophenyl)-1-nitropropane.
Yield: 88%
(R)/(S)=95/5

Example 5

The same procedure as Example 4, except that 10 μmol of the asymmetric copper complex of (S)—(R)-JOSIPHOS was used in place of 1 μmol of the asymmetric copper complex of (S)—(R)-JOSIPHOS, provided optically active 2-(4-chlorophenyl)-1-nitropropane.
Yield: 89%
(R)/(S)=95/5

Example 6

The same procedure as Example 5, except that (E)-2-(4-methoxyphenyl)-1-nitro-1-propene was used in place of (E)-2-(4-chlorophenyl)-1-nitro-1-propene, provided optically active 2-(4-methoxyphenyl)-1-nitropropane.
Yield: 94%
(R)/(S)=95/5

¹H-NMR (δ, 300 MHz, CDCl₃, 25° C.) 7.15 (m, 2H), 6.87 (m, 2H), 4.51 (dd, J=11.8, 8.1 Hz, 1H), 4.45 (dd, J=11.8, 8.1 Hz, 1H), 3.79 (s, 3H), 3.59 (m, 1H), 1.36 (d, J=7.2 Hz, 3H)

Example 7

The same procedure as Example 5, except that (E)-3-hydroxy-2,3-dimethyl-1-nitro-1-butene was used in place of (E)-2-(4-chlorophenyl)-1-nitro-1-propene, provided optically active 3-hydroxy-2,3-dimethyl-1-nitrobutane.
Yield: 66%
(R)/(S)=95/5

Example 8

The same procedure as Example 7, except that 3 μmol of the asymmetric copper complex of (S)-(R)-JOSIPHOS was used in place of 10 μmol of the asymmetric copper complex of (S)—(R)-JOSIPHOS, provided optically active 3-hydroxy-2,3-dimethyl-1-nitrobutane.
Yield: 55%
(R)/(S)=97/3

Example 9

The same procedure as Example 7, except that (S)-p-tol-BINAP was used in place of (S)—(R)-JOSIPHOS, provided optically active 3-hydroxy-2,3-dimethyl-1-nitrobutane.
Yield: 60%
(R)/(S)=93/7

Example 10

The same procedure as Example 9, except that (Z)-2-methyl-1-nitro-3-tetrahydropyranyloxy-1-propene was used in place of (E)-3-hydroxy-2,3-dimethyl-1-nitro-1-butene, provided optically active 2-methyl-1-nitro-3-tetrahydropyranyloxypropane.
Yield: 76%
(R)/(S)=83/17

Example 11

The same procedure as Example 10, except that (S)—(R)-JOSIPHOS was used in place of (S)-p-tol-BINAP, provided optically active 2-methyl-1-nitro-3-tetrahydropyranyloxypropane.
Yield: 62%
(R)/(S)=93/7

Example 12

The same procedure as Example 11, except that 1 μmol of the asymmetric copper complex of (S)-(R)-JOSIPHOS was used in place of 10 μmol of the asymmetric copper complex of (S)—(R)-JOSIPHOS, provided optically active 2-methyl-1-nitro-3-tetrahydropyranyloxypropane.
Yield: 81%
(R)/(S)=93/7

Example 13

The same procedure as Example 11, except that (E)-2-methyl-1-nitro-3-tetrahydropyranyloxy-1-propene was used in place of (Z)-2-methyl-1-nitro-3-tetrahydropyranyloxy-1-propene, provided optically active 2-methyl-1-nitro-3-tetrahydropyranyloxypropane.
Yield: 82%
(R)/(S)=84/16

Example 14

The same procedure as Example 12, except that (E)-2-methyl-1-nitro-3-tetrahydropyranyloxy-1-propene was used in place of (Z)-2-methyl-1-nitro-3-tetrahydropyranyloxy-1-propene, provided optically active 2-methyl-1-nitro-3-tetrahydropyranyloxypropane.
Yield: 77%
(R)/(S)=83/17

Example 15

The same procedure as Example 5, except that (Z)-3-methyl-1-nitro-2-phenyl-1-butene was used in place of (E)-2-(4-chlorophenyl)-1-nitro-1-propene, provided optically active 3-methyl-1-nitro-2-phenylbutane.
Yield: 83%
(R)/(S)=97/3

Example 16

The same procedure as Example 5, except that (E)-1-nitro-2-phenyl-1-pentene was used in place of (E)-2-(4-chlorophenyl)-1-nitro-1-propene, provided optically active 1-nitro-2-phenyl-1-pentane.
Yield: 86%
(R)/(S)=96/4

Example 17

In a 10 mL Schlenk-flask, 6.8 mg of copper (I) tert-butoxide and 55 μmol of (S)—(R)-JOSIPHOS were dissolved in 5 ml of toluene. After stirring for 30 minutes at room temperature to give an asymmetric copper complex. This solution to the amount containing 10 μmol of the asymmetric copper complex were mixed with 4.9 ml of toluene, and 6 μL (0.1 mmol) of poly(methylhydrosiloxane) (15-40 mPas (20° C.), d=1.004 g/mL, nD20=1.398, produced by Fluka) were added thereto. Further, 185 μL of (1.5 mmol) of phenylsilane and 27 μL (1.5 mmol) of water were added. After stirring for 5 minutes, 1 mmol of (E)-1-nitro-2-(pyridin-2-yl)-1-propene was added, and the mixture was further stirred for 24 hours at room temperature. Water was added to the reaction mixture and the product was extracted with diethyl ether (30 mL×2). After drying over sodium sulfate, the solvent was evaporated. The residue was purified by flash chromatography (silica gel, hexane/ethyl acetate) to provide optically active 1-nitro-2-(pyridin-2-yl)propane.
Yield: 55%
(R)/(S)=86/14

Example 18

The same procedure as Example 5, except that (E)-1-nitro-2-(furan-2-yl)-1-propene was used in place of (E)-2-(4-chlorophenyl)-1-nitro-1-propene, provided optically active 1-nitro-2-(furan-2-yl)propane.
Yield: 72%
(R)/(S)=95/5

Example 19

The same procedure as Example 5, except that (E)-1-nitro-2-(thiophen-2-yl)-1-propene was used in place of (E)-2-(4- chlorophenyl)-1-nitro-1-propene, provided optically active 1-nitro-2-(thiophen-2-yl)propane.
Yield: 73%
(R)/(S)=92/8

Example 20

The same procedure as Example 17, except that (E)-3-hydroxy-1-nitro-2-phenyl-1-propene was used in place of (E)-1-nitro-2-(pyridin: 2-yl)-1-propene, provided optically active 3-hydroxy-1-nitro-2-phenylpropane.
Yield: 55%
(R)/(S)=96/4

Example 21

The same procedure as Example 17, except that (Z)-3-hydroxy-1-nitro-2-phenyl-1-propene was used in place of (E)-1-nitro-2-(pyridin-2-yl)-1-propene, provided optically active 3-hydroxy-1-nitro-2-phenylpropane.
Yield: 70%
(R)/(S)=94/6

Example 22

The same procedure as Example 5, except that (Z)-1-nitro-2-phenyl-3-trifluoroacetamino-1-propene was used in place of (E)-2-(4-chlorophenyl)-1-nitro-1-propene, provided optically active 1-nitro-2-phenyl-3-(trifluoroacetamino)propane.
Yield: 73%
(R)/(S)=89/11

Example 23

The same procedure as Example 5, except that (Z)-3-benzoylamino-1-nitro-2-phenyl-1-propene was used in place of (E)-2-(4-chlorophenyl)-1-nitro-1-propene, provided optically active 3-(benzoylamino)-1-nitro-2-phenylpropane.
Yield: 70%
(R)/(S)=95/5

Example 24

In a 10 mL Schlenk-flask, 6.8 mg of copper (I) tert-butoxide and 55 µmol of (S)—(R)-JOSIPHOS were dissolved in 5 ml of toluene. After stirring for 30 minutes at room temperature to give an asymmetric copper complex. This solution to the amount containing 10 µmol of the asymmetric copper complex were mixed with 4.9 ml of toluene. Further, 185 µL of (1.5 mmol) of phenylsilane and 27 µL (1.5 mmol) of water were added thereto. After stirring for 5 minutes, 1 mmol of (E)-2-(4-acetylphenyl)-1-nitro-1-propene was added, and the mixture was further stirred for 24 hours at room temperature. Four milliliters (4 mL) of a tetrahydrofuran solution of tetrabutylammonium fluoride (1 mol/L) were added to the reaction mixture and stirring was continued for 3 hours. Water was added and the mixture was extracted with diethyl ether (30 mL×2). After drying over sodium sulfate, the solvent was evaporated. The residue was purified by flash chromatography (silica gel, hexane/ethyl acetate) to provide optically active 2-(4-acetylphenyl)-1-nitropropane.
Yield: 86%
(R)/(S)=95/5

Example 25

In a 10 mL Schlenk-flask, 8 mg of copper (I) chloride and 8 mg of sodium tert-butoxide and 110 mg of (S)-p-tol-BINAP were dissolved in 6 ml of toluene. After stirring for 15 minutes at room temperature to give an asymmetric copper complex. Into this solution, 360 µL (6.0 mmol) of poly(methylhydrosiloxane) (15-40 mPas (20° C.), d=1.004 g/mL, nD20=1.398, produced by Fluka) and 32 mg of water were added. After stirring for 5 minutes, 1.5 mmol of (E)-1-nitro-2-phenyl-1-propene were added, and the mixture was further stirred for 22 hours at room temperature. $^1$H-NMR analysis showed that the objective optically active 1-nitro-2-phenylpropane was provided in 50% yield. A by-product, 1-nitro-2-phenyl-2-propene was provided in 4% yield.

The reduction of the nitro compound obtained by the above-mentioned method for producing the optically active amino compound is given by the following example.

Example 26

Under argon atmosphere, 121 mg of optically active 1-nitro-2-phenylpropane (732 µmol) were dissolved in 5 mol of dry methanol and 50 mg of palladium on charcoal (10%) were added thereto. The obtained suspension was vigorously stirred under hydrogen atmosphere for 24 hours. The mixture was filtered and the solid was washed with methanol. The solvent was evaporated and the residue was dissolved in 2 ml of benzene. The solvent was evaporated to give 95 mg of an optically active 1-amino-2-phenylpropane as a colorless oil (703 µmol).
Yield: 96%

INDUSTRIAL APPLICABILITY

The present invention provides a method for producing optically active nitro compounds and amino compounds which are useful for synthetic intermediates for fine chemicals, medicaments, pesticides and so on.

The invention claimed is:

1. A method for producing an optically active nitro compound having two hydrogen atoms on its α-carbon atom and having β-asymmetric carbon atom which comprises making α,β-unsaturated nitroolefin having a hydrogen atom on its α-carbon atom react with at least two organosilicon compounds having at least one silicon-hydrogen bond in the molecule in the presence of an asymmetric copper complex by mixing the nitroolefin and the organosilicon compounds at −78° to 100° C.

2. The method according to claim 1, wherein the organosilicon compounds are poly(methylhydrosiloxane) and at least one selected from the group consisting of phenylsilane, diphenylsilane and dimethylphenylsilane.

3. The method according to claim 1, wherein the asymmetric copper complex has at least one optically active bidentate phosphine ligand.

4. The method according to claim 1, wherein the nitro compound is a compound of formula (1):

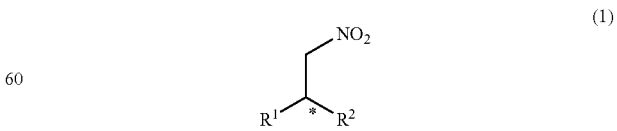

wherein $R^1$ and $R^2$ are different from each other, and each of $R^1$ and $R^2$ represents an optionally substituted C1-C10 alkyl group, optionally substituted C3-C10 cycloalkyl group, optionally substituted C6-C14 aryl group or optionally substituted heterocyclic group; said heterocyclic group is pyridyl group, pyrimidinyl group, furyl group, thienyl group, pyrazolyl group, imidazolyl group, oxazolyl group, thiazolyl group, quinolyl group, quinazolinyl group, dihydropyridyl group, tetrahydrofuranyl group and piperidyl group; and the substituent of the alkyl group, cycloalkyl group, aryl group and heterocyclic group is one or more selected from the group consisting of halogen atom, hydroxyl group, cyano group, isocyano group, C1-C10 alkoxy group, C3-C10 cycloalkyl group, C6-C14 aryl group, C1-C10 alkylcarbonyl group, C6-C14 haloaryl group, C1-C10 alkylcarbonyloxy group, benzyloxy group, halobenzyloxy group, C1-C10 alkylsulfonyloxy group, C6-C14 arylsulfonyloxy group, C6-C14 haloarylsulfonyloxy group, tetrahydrofuranyloxy group, tetrahydropyranyloxy group, amino group, C1-C10 alkylcarbonylamino group, trifluoroacetamino group, C6-C14 arylcarbonylamino group, halobenzoylamino group, benzyloxycarbonylamino group, pyridyl group, pyrimidinyl group, furyl group, thienyl group, imidazolyl group, halopyridyl group, C1-C10 alkylpyridyl group and C1-C10 alkylfuryl group; and * indicates an asymmetric carbon, and the α,β-unsaturated nitroolefin is a compound of formula (2):

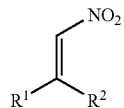

(2)

wherein R¹ and R² have the same meanings given above.

5. A method for producing optically active nitro compound having two hydrogen atoms on its α-carbon atom and having β-asymmetric carbon atom which comprises making α,β-unsaturated nitroolefin having a hydrogen atom on its α-carbon atom react with an organosilicon compound having at least one silicon-hydrogen bond in the molecule in the presence of an asymmetric copper complex and water by mixing the nitroolefin and the organosilicon compound at −78° C. to 100° C.

6. The method according to claim 5, wherein the asymmetric copper complex has at least one optically active bidentate phosphine ligand.

7. The method according to claim 5, wherein the nitro compound is a compound of formula (1):

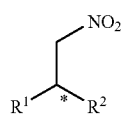

(1)

wherein R¹ and R² are different from each other, and each of R¹ and R² represents an optionally substituted C1-C10 alkyl group, optionally substituted C3-C10 cycloalkyl group, optionally substituted C6-C14 aryl group or optionally substituted heterocyclic group; said heterocyclic group is pyridyl group, pyrimidinyl group, furyl group, thienyl group, pyrazolyl group, imidazolyl group, oxazolyl group, thiazolyl group, quinolyl group, quinazolinyl group, dihydropyridyl group, tetrahydrofuranyl group and piperidyl group; and the substituent of the alkyl group, cycloalkyl group, aryl group and heterocyclic group is one or more selected from the group consisting of halogen atom, hydroxyl group, cyano group, isocyano group, C1-C10 alkoxy group, C3-C10 cycloalkyl group, C6-C14 aryl group, C1-C10 alkylcarbonyl group, C6-C14 haloaryl group, C1-C10 alkylcarbonyloxy group, benzyloxy group, halobenzyloxy group, C1-C10 alkylsulfonyloxy group, C6-C14 arylsulfonyloxy group, C6-C14 haloarylsulfonyloxy group, tetrahydrofuranyloxy group, tetrahydropyranyloxy group, amino group, C1-C10 alkylcarbonylamino group, trifluoroacetamino group, C6-C14 arylcarbonylamino group, halobenzoylamino group, benzyloxycarbonylamino group, pyridyl group, pyrimidinyl group, furyl group, thienyl group, imidazolyl group, halopyridyl group, C1-C10 alkylpyridyl group and C1-C10 alkylfuryl group; and * indicates an asymmetric carbon, and the α,β-unsaturated nitroolefin is a compound of formula (2):

(2)

wherein R¹ and R² have the same meanings given above.

8. A method for producing an optically active amino compound which comprises reducing an optically active nitro compound having two hydrogen atoms on its α-carbon atom and having β-asymmetric carbon atom obtained by making α,β-unsaturated nitroolefin having a hydrogen atom on its α-carbon atom react with at least two organosilicon compounds having at least one silicone-hydrogen bond in the molecule in the presence of an asymmetric copper complex, or with an organosilicon compound having at least one silicon-hydrogen bond in the molecule in the presence of an asymmetric copper complex and water by mixing the nitroolefin and the organosilicon compound or compounds at −78° C. to 100° C.

9. The method according to claim 1, wherein the optically active nitro compound is 1-amino-2-phenylpropane, 1-amino-2-(4-methylphenyl)propane, 1-amino-2-(4-chlorophenyl)propane, 1-amino-2-(4-methoxyphenyl)propane, 2-(4-acetylphenyl)-1-aminopropane, 1-amino-2-(4-trifluoromethylphenyl)propane, 1-amino-3-methyl-2-phenylbutane, 1-amino-3-hydroxy-2-phenylpropane, 1-amino-2,3,3-trimethylbutane, 1-amino-3-hydroxy-2,3-dimethylbutane, 1-amino-2,4,4-trimethylpentane, 1-amino-2-phenylpentane, 1-amino-2-(2-naphthyl)propane, 1-amino-3-(benzoylamino)-2-phenylpropane, 3-acetamino-1-amino-2-phenylpropane, 1-amino-3-(trifluoroacetamino)-2-phenylpropane, 1-amino-2-(pyridin-2-yl)propane, 1-amino-2-(5-chloropyridin-2-yl)propane, 1-amino-2-[(pyridin-2-yl)methyl]propane, 1-amino-2-(furan-2-yl)propane, 1-amino-2-furfurylpropane, 1-amino-2-(thiophen-2-yl)propane, 1-amino-2-[(tetrahydropyranyloxy)methyl]propane or 1-amino-2-[(tetrahydrofurfuryloxy)methyl]propane.

10. The method according to claim 5, wherein the optically active nitro compound is 1-amino-2-phenylpropane, 1-amino-2-(4-methylphenyl)propane, 1-amino-2-(4-chlorophenyl)propane, 1-amino-2-(4-methoxyphenyl)propane, 2-(4-acetylphenyl)-1-aminopropane, 1-amino-2-(4-trifluoromethylphenyl)propane, 1-amino-3-methyl-2-phenylbutane, 1-amino-3-hydroxy-2-phenylpropane, 1-amino-2,3,3-trimethylbutane, 1-amino-3-hydroxy-2,3-dimethylbutane, 1-amino-2,4,4-trimethylpentane, 1-amino-2-phenylpentane, 1-amino-2-(2-naphthyl)propane, 1-amino-3-(benzoylamino)-2-phenylpropane, 3-acetamino-1-amino-2-phenylpropane, 1-amino-3-(trifluoroacetamino)-2-phenylpropane, 1-amino-2-(pyridin-2-yl)propane, 1-amino-2-(5-chloropyridin-2-yl)propane, 1-amino-2-[(pyridin-2-yl)methyl]propane, 1-amino-2-(furan-2-yl)propane, 1-amino-2-furfurylpropane, 1-amino-2-(thiophen-2-yl)propane, 1-amino-2-[(tetrahydropyranyloxy)methyl]propane or 1-amino-2-[(tetrahydrofurfuryloxy)methyl]propane.

11. The method according to claim 8, wherein the optically active nitro compound is 1-amino-2-phenylpropane, 1-amino-2-(4-methylphenyl)propane, 1-amino-2-(4-chlorophenyl)propane, 1-amino-2-(4-methoxyphenyl)propane, 2-(4-acetylphenyl)-1-aminopropane, 1-amino-2-(4-trifluoromethylphenyl)propane, 1-amino-3-methyl-2-phenylbutane, 1-amino-3-hydroxy-2-phenylpropane, 1-amino-2,3,3-trimethylbutane, 1-amino-3-hydroxy-2,3-dimethylbutane, 1-amino-2,4,4-trimethylpentane, 1-amino-2-phenylpentane, 1-amino-2-(2-naphthyl)propane, 1-amino-3-(benzoylamino)-2-phenylpropane, 3-acetamino-1-amino-2-phenylpropane, 1-amino-3-(trifluoroacetamino)-2-phenylpropane, 1-amino-2-(pyridin-2-yl)propane, 1-amino-2-(5-chloropyridin-2-yl)propane, 1-amino-2-[(pyridin-2-yl)methyl]propane, 1-amino-2-(furan-2-yl)propane, 1-amino-2-furfurylpropane, 1-amino-2-(thiophen-2-yl)propane, 1-amino-2-[(tetrahydropyranyloxy)methyl]propane or 1-amino-2-[(tetrahydrofurfuryloxy)methyl]propane.

\* \* \* \* \*

UNITED STATES PATENT AND TRADEMARK OFFICE
CERTIFICATE OF CORRECTION

| | | |
|---|---|---|
| PATENT NO. | : 7,790,900 B2 | Page 1 of 1 |
| APPLICATION NO. | : 10/556777 | |
| DATED | : September 7, 2010 | |
| INVENTOR(S) | : Erick M. Carreira | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1172 days.

Signed and Sealed this
Fifth Day of April, 2011

David J. Kappos
*Director of the United States Patent and Trademark Office*